US007163672B2

(12) United States Patent
Buckton et al.

(10) Patent No.: US 7,163,672 B2
(45) Date of Patent: Jan. 16, 2007

(54) PHARMACEUTICAL AEROSOL FORMULATION

(75) Inventors: Graham Buckton, London (GB); Angela Columbano, Walton-on-Thames (GB); Martin Grosvenor, Loughborough (GB); Philip Wikeley, Whittington (GB)

(73) Assignee: AstraZeneca AB, Södertälje (SE)

( * ) Notice: Subject to any disclaimer, the term of this patent is extended or adjusted under 35 U.S.C. 154(b) by 271 days.

(21) Appl. No.: 10/451,162

(22) PCT Filed: Dec. 19, 2001

(86) PCT No.: PCT/SE01/02853

§ 371 (c)(1),
(2), (4) Date: Nov. 25, 2003

(87) PCT Pub. No.: WO02/49616

PCT Pub. Date: Jun. 27, 2002

(65) Prior Publication Data

US 2004/0082520 A1    Apr. 29, 2004

(30) Foreign Application Priority Data

Dec. 19, 2000  (SE)  .................................. 0004750

(51) Int. Cl.
*A61L 9/00*   (2006.01)
*A61L 9/14*   (2006.01)
*A61K 31/7016*   (2006.01)
*A61K 31/702*   (2006.01)

(52) U.S. Cl. .............................. 424/45; 514/25; 514/61

(58) Field of Classification Search ................. 424/45; 514/25, 61
See application file for complete search history.

(56) References Cited

U.S. PATENT DOCUMENTS 6,080,387 A * 6/2000 Zhou et al. .................... 424/45
6,080,869 A * 6/2000 Bonnert et al. ............. 548/169
6,143,277 A * 11/2000 Ashurst et al. ................ 424/45
6,482,392 B1* 11/2002 Zhou et al. .................... 424/45

FOREIGN PATENT DOCUMENTS

| WO | WO 95/00151 | 1/1995 |
| WO | WO 96/19198 | 6/1996 |
| WO | WO 97/47286 | 12/1997 |
| WO | WO 98/30244 | 7/1998 |
| WO | WO 00/19980 | 4/2000 |

OTHER PUBLICATIONS

CAPLUS Abstract, "Alkyl glucoside-based aerosol type foam products," Ascension No. 1997:328726, document No. 126:306557, corresponding to Japanese Patent JP 09059606, published Mar. 4, 1997.

* cited by examiner

Primary Examiner—Johann R. Richter
Assistant Examiner—James Henry Alstrum-Acevedo
(74) Attorney, Agent, or Firm—Fish & Richardson P.C.

(57) ABSTRACT

The invention relates to a pharmaceutical aerosol formulation comprising a surfactant that is an alkyl-polyglycoside of formula I, wherein DP is the average degree of polymerisation and has a value of from 1 to 4, and R is an alkyl chain or a mixture of alkyl chains having a chain length of from 6 to 22 carbon atoms; or a derivative thereof for the administration of a medicament for inhalation.

31 Claims, 8 Drawing Sheets

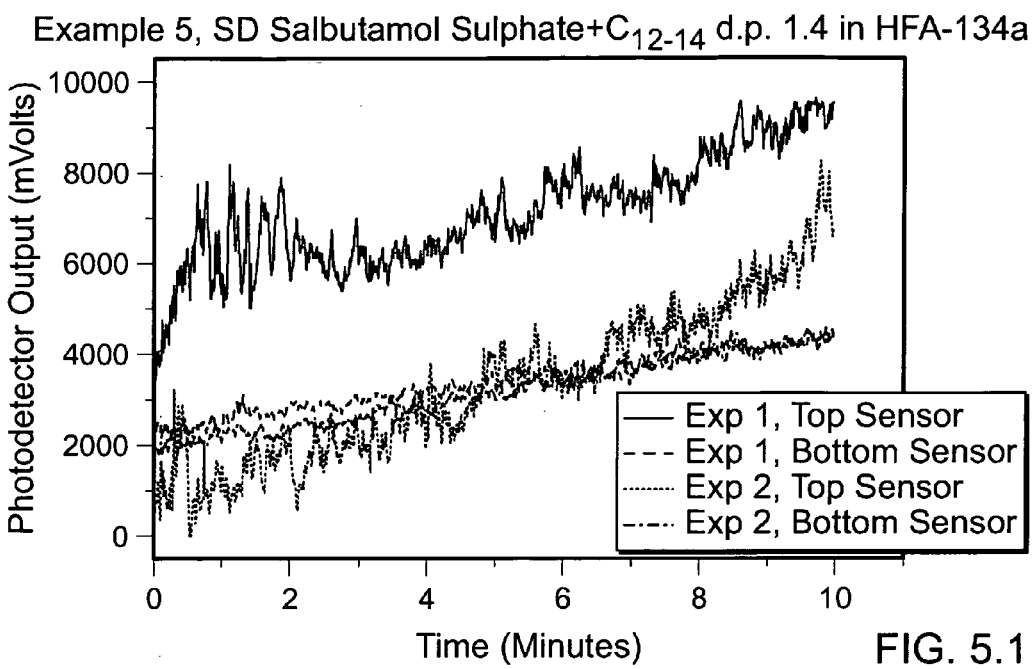
FIG. 5.1
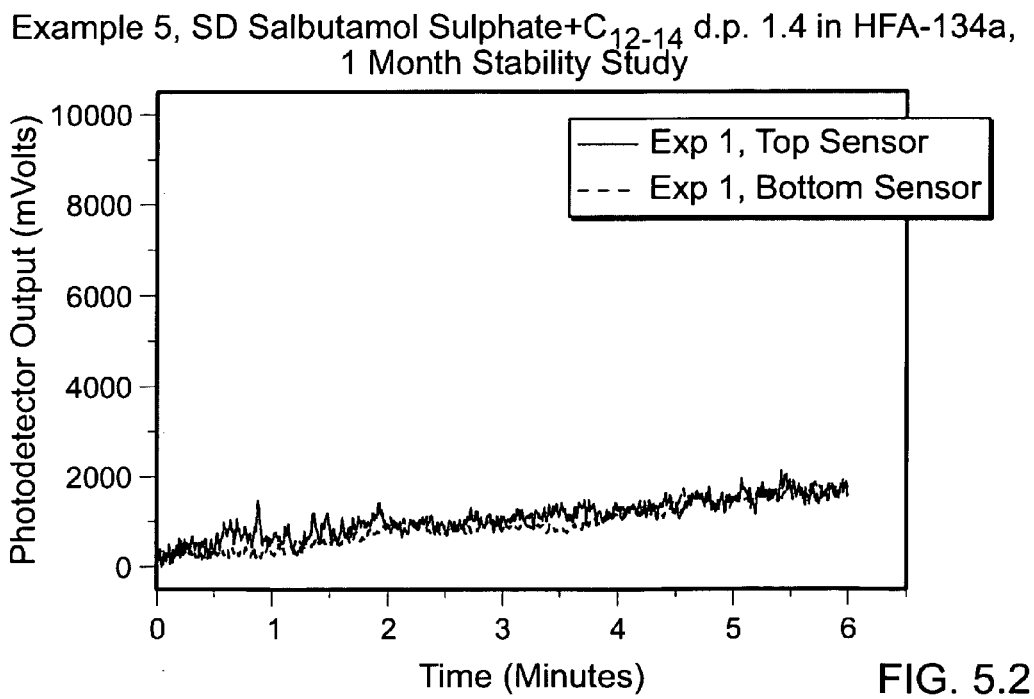
FIG. 5.2

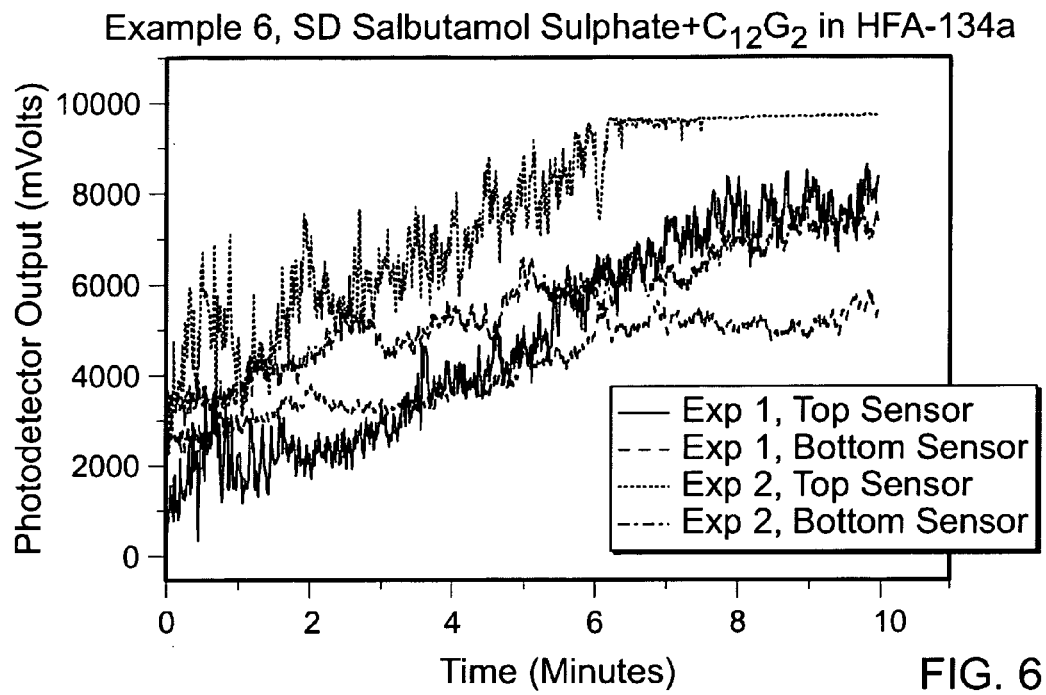
FIG. 6.1
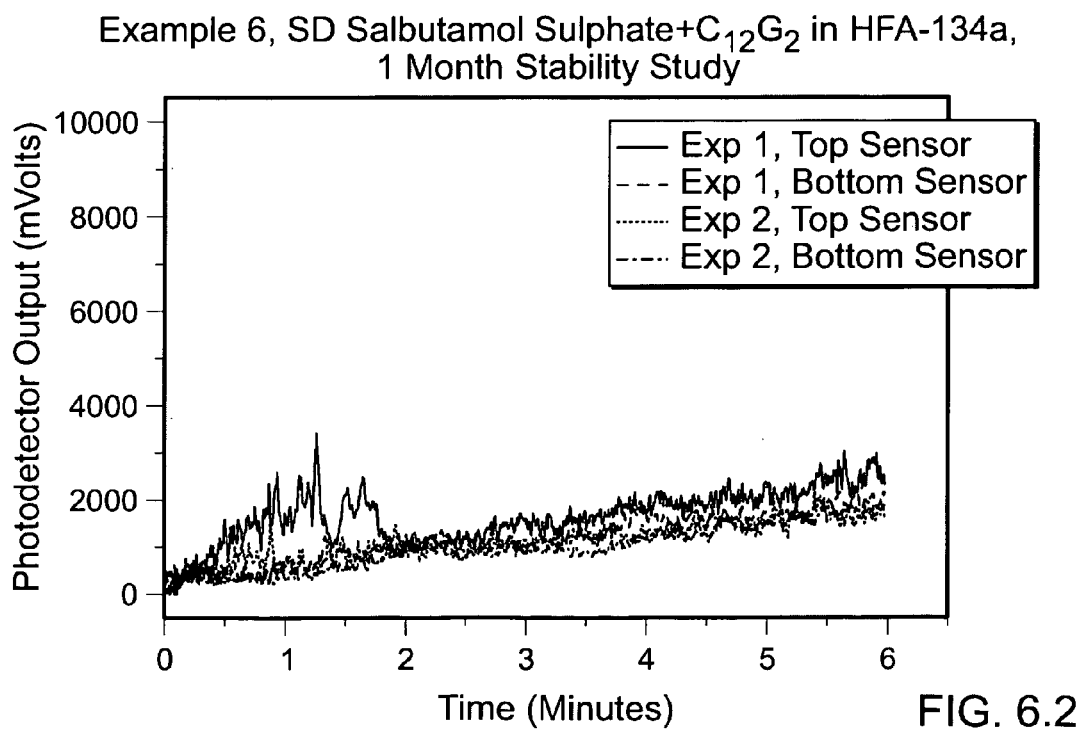
FIG. 6.2

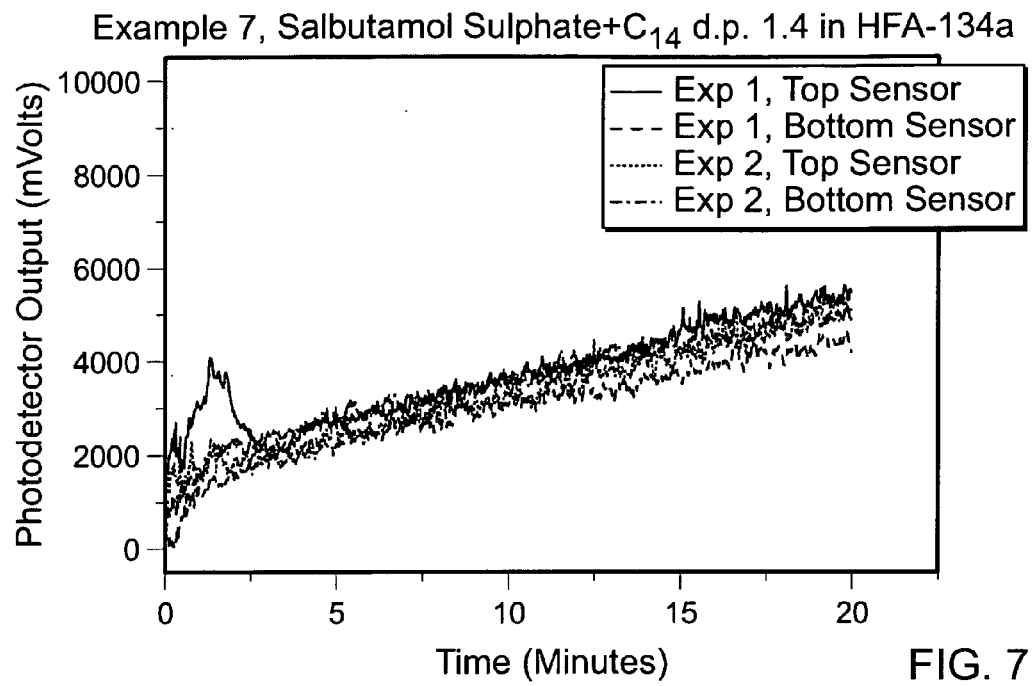
FIG. 7.1
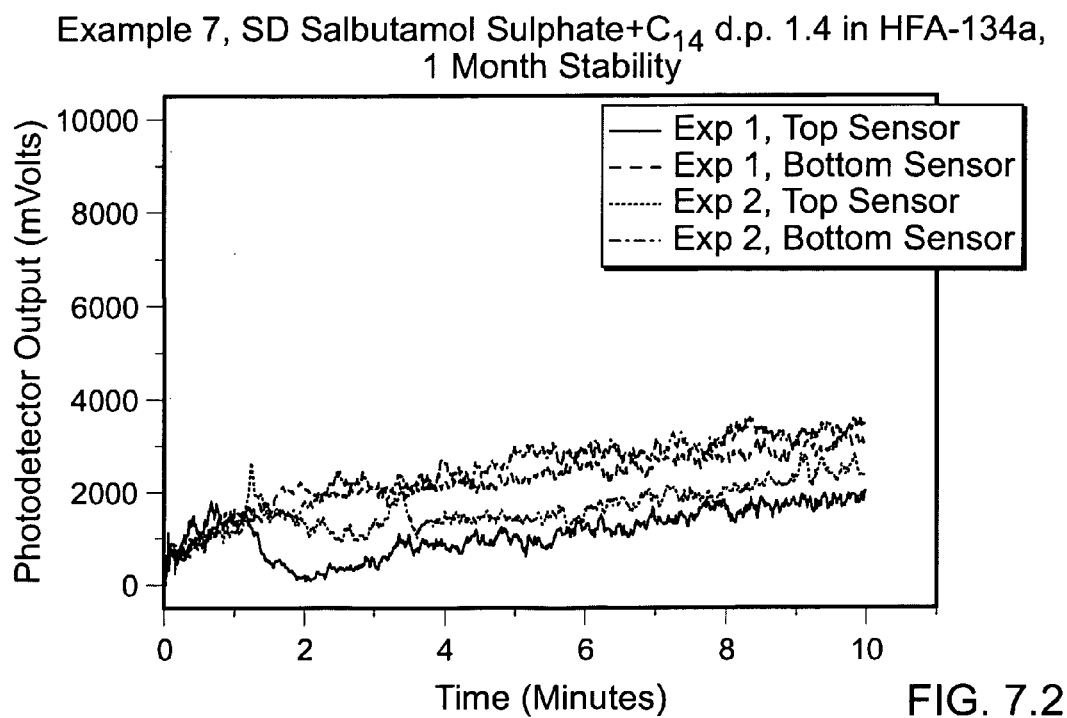
FIG. 7.2

Control 3, Spray Dried Salbutamol Sulphate in HFA-134a

FIG. 10

Control 3, Spray Dried Salbutamol Sulphate in HFA-134a, 1 Month Stability Study

FIG. 11

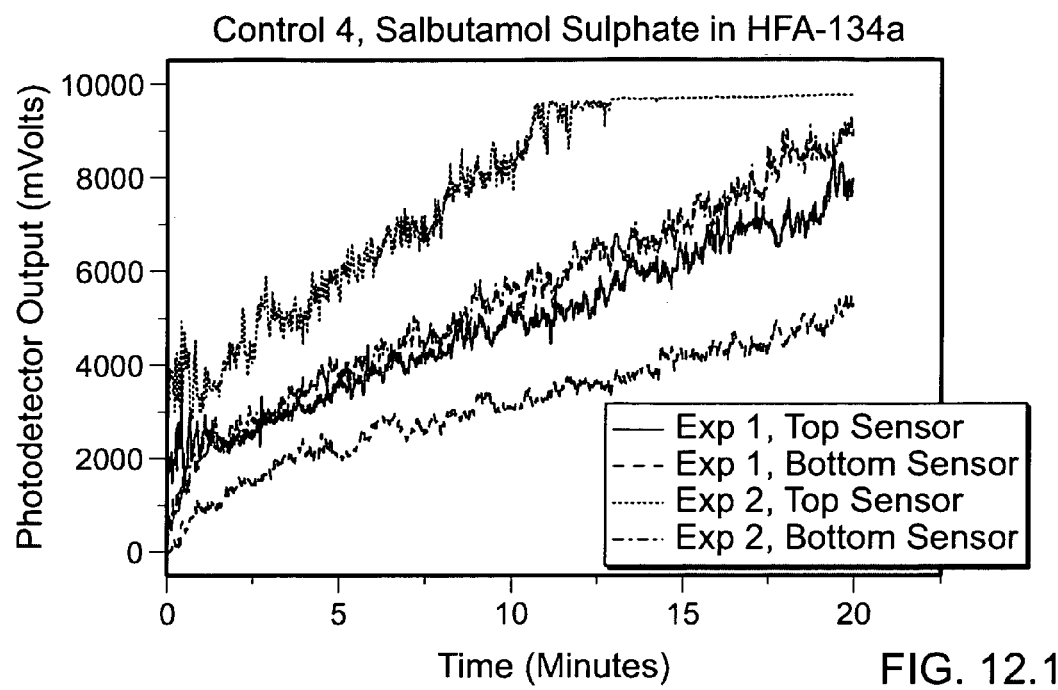
FIG. 12.1
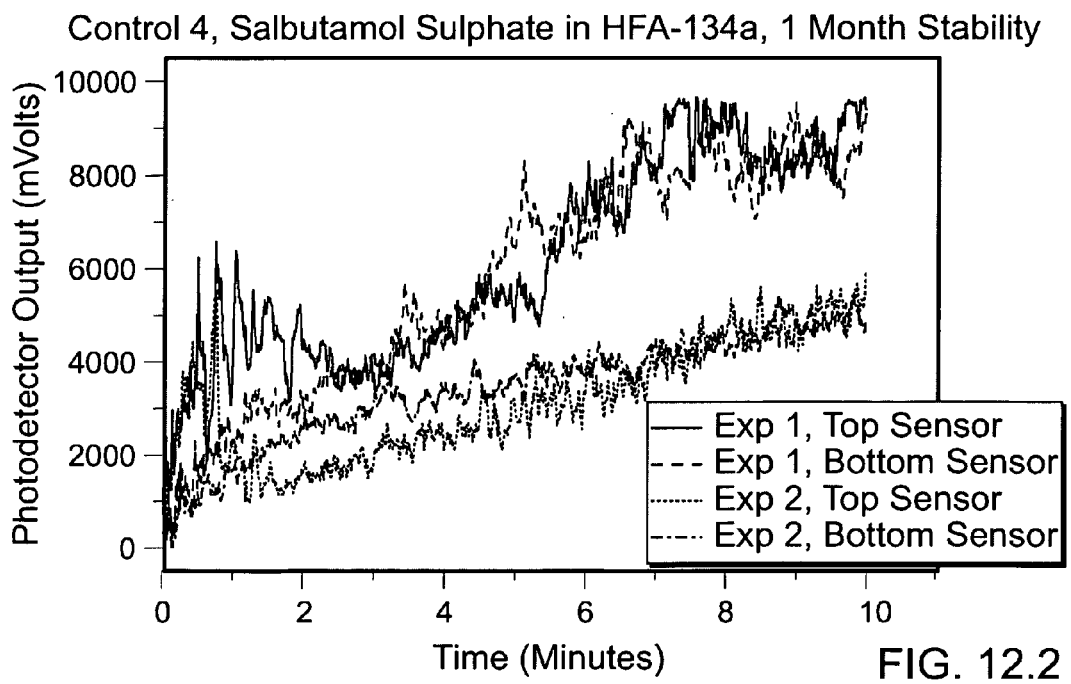
FIG. 12.2

PHARMACEUTICAL AEROSOL FORMULATION

This application, filed Nov. 25, 2003, under 35 USC § 371, is a national phase application of PCT/SE01/02853 filed Dec. 19, 2001, which claims priority to Swedish patent application 0004750-6, filed Dec. 19, 2000. The disclosures of the prior applications are considered part of (and are incorporated by reference in) the disclosure of this application.

The present invention relates to a pharmaceutical aerosol formulation for the administration of a medicament for inhalation.

Drugs for treating respiratory and nasal disorders are frequently administered in aerosol formulations through the mouth or nose. One widely used method for dispensing such an aerosol formulation involves making a suspension formulation of the drug as a finely divided powder in a liquefied propellant gas. Alternatively a solution formulation can be prepared where the drug is dissolved in a propellant system, perhaps containing solubilisers and co-solvents to aid dissolution of the drug. Pressurised metered dose inhalers (pMDIs) are normally used to dispense such formulations to a patient Surface active agents, or surfactants, are commonly included in order to aid dispersion of the drug in the propellant and to prevent aggregation of the drug particles, and to improve lubrication. In solution formulations they are used to help solubilise the drug. Following the implication of chlorofluorocarbon (CFC) propellants in the destruction of the ozone layer, CFCs are being replaced by hydrofluoroalkane (HFA) propellants. However the range of surfactants commonly used in the CFC systems have proven to be generally unsuitable for use in HFA systems. Various alternative surfactants have been proposed.

For example, WO92/00061 discloses polyethoxylated surfactants for use with HFA propellants. WO91/11173 discloses fluorinated surfactants. WO91/14422 discloses perfluorinated carboxylic acid surfactants for use with HFA propellants. WO92/00107 discloses the use of a propellant-soluble surfactant with propellant 134a, 1,1,1,2-tetrafluoroethane. WO96/19198 discloses aerosol formulations comprising a HFA propellant, a medicament for inhalation and a surfactant which is a $C_{8-16}$ fatty acid or salt thereof, a bile salt, a phospholipid, or an alkyl saccharide.

We have found a class of surfactants which are particularly suitable for use in hydrofluoroalkane propellant systems. Said surfactants are highly surface active and allow the generation of dispersion or solution formulations with HFA propellants. Further advantages of the said surfactants are their low ecotoxicity, and the ability to synthesise ranges of surfactants with a range of properties such as Molecular Weight, degree of polymerisation.

The present invention provides a pharmaceutical aerosol formulation comprising a hydrofluoroalkane propellant, a medicament for inhalation and a surfactant, characterised in that the surfactant is an alkyl-polyglycoside of formula I:

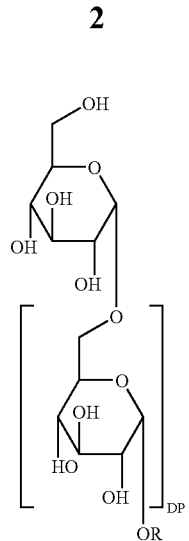

wherein DP is the average degree of polymerisation and has a value of from 1 to 4, and R is an alkyl chain or a mixture of alkyl chains having a chain length of from 6 to 22 carbon atoms; or a derivative thereof.

The alkyl chain R may be linear or branched and may, for example, be derived from a primary, secondary or tertiary alcohol.

Derivatives of the alkylpolyglycosides of formula I include butyl ethers, carbonates and sulfo-succinates.

The nomenclature for alkylpolyglycosides is $C_nG_m$ for "pure surfactants" where n is defined as the number of carbon atoms in the alkyl chain and m the number of glucose units attached as the head group. The term "pure" is a relative one as the pure surfactants are not pure in surface chemistry terms but are more homogeneous than technical grade surfactants. Technical grade surfactants are described by a range of alkyl chain lengths ($C_{a-b}$) as they are derived from natural alcohols, which have a range of alkyl chain lengths and an average number of glucose groups per molecule which is expressed as a degree of polymerisation (d.p.). Thus $C_{10-12}$ d.p. 1.4 has a range of alkyl chain from decyl to dodecyl and an average of 1.4 glucose units per alkyl chain in the sample.

"BEROL AG6202™" (Chemical Abstracts Registry number 201491-13-6) from Akzo Nobel, an alkylpolyglycoside (2-ethyl-1-hexylglycoside) of formula I in which R is 2-ethyl-1-hexyl and DP is 1.6;

"GLUCOPON 215CS™" (Chemical Abstracts Registry number 208852-94-2) from Henkel, an alkylpolyglycoside of formula I in which R is a mixture of $C_8$ and $C_{10}$ alkyl chains in a ratio of 60 $C_8$: 40 $C_{10}$ and DP is 1.5;

"MONTANOV 68™" (Chemical Abstracts Registry number 156410-05-8) from SEPPIC, an alkylpolyglycoside of formula I in which R is a mixture of $C_{16}$ and $C_{18}$ alkyl chains and DP is 1.2–1.3; and "MONTANOV 202™" (Chemical Abstracts Registry number 100231-68-3) from SEPPIC, an alkylpolyglycoside of formula I in which R is a mixture of $C_{20}$ and $C_{22}$ alkyl chains and DP is 1.2–1.3.

n-dodecyl β-D-maltoside ($C_{12}G_2$) is available from Sigma. $C_{10}$ d.p 2.7 is available from Akzo-Nobel $C_{10-12}$ d.p. 1.4 and $C_{12-14}$ d.p. 1.4 are available from Henkel The propellant may be any of hydrofluoroalkane propellant; preferred propellants include 1,1,1,2-tetrafluoroethane (HFA-134a), 1,1,1,2,3,3,3-heptafluoropropane (HFA-227ea) and a mixture of HFA-134a and HFA-227ea, for example a density matched mixture of HFA-134a and HFA-227ea.

Medicaments suitable for inclusion in the formulation of the present invention are any which may be delivered by inhalation.

Suitable inhalable medicaments may include for example β2-adrenoreceptor agonists for example salbutamol, terbutaline, rimiterol, fenoterol, reproterol, adrenaline, pirbuterol, isoprenaline, orciprenaline, bitolterol, salmeterol, formoterol, clenbuterol, procaterol, broxaterol, picumeterol, TA-2005 and malbuterol; anticholinergic bronchodilators for example ipratropium bromide, oxitropium and its salts and tiotropium and its salts; glucocorticosteroids for example beclomethasone, fluticasone, budesonide, tipredane, dexamethasone, betamethasone, fluocinolone, triamcinolone acetonide, flunisolide, mometasone and 16, 17-acetals of pregnane derivatives, for example rofleponide palmitate and ciclesonide; anti-allergic medicaments for example sodium cromoglycate and nedocromil sodium; leukotriene antagonists for example, zafirlukast, montelukast, pranlukast, zileuton antihistamines for example terfenadine, cetirizine, loratadine and azelastine; antibiotics; pain control substances, for example morphine, codeine, pethidine, etc.

According to one embodiment of the pharmaceutical aerosol formulation, the medicament is a compound of formula:

$$Ar-CH_2-CH_2-NH-CR^1R^2-A-Z$$

in which Ar represents a group

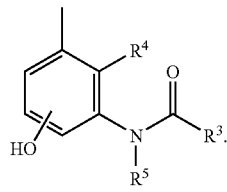

A represents a $C_{1-12}$ alkylene chain which may be straight or branched and which is interrupted or terminated by one or more groups selected from —S—, —SO—, $SO_2$—, —O—, $SO_2NH$, $NHSO_2$, $CR^6R^7$, phenylmethyne, —NH—, —CONH—, —NHCO— and —NH-CONH—;

Z represents an aryl group of five or six atoms, in a single ring system, which may contain from 1 to 3 heteroatoms selected from N, O and S, which single ring system may be optionally substituted to form a multiple fused ring system of up to 10 atoms, the aryl group being optionally substituted by one or more groups selected from —OH, halogen, $C_{1-6}$ alkyl, $C_{1-6}$ alkoxy, =O, —$NR^8R^9$, $NO_2$, and a $C_{3-12}$ cycloalkyl group which may contain from 1 to 3 heteroatoms selected from N, O and S, optionally substituted by one or more groups selected from —OH, halogen, $C_{1-6}$ alkyl, $C_{1-6}$ alkoxy, =O, —$NH_2$, and $NO_2$;

$R^1$, $R^2$, $R^5$, $R^6$, $R^7$, $R^8$ and $R^9$ each independently represent hydrogen or $C_{1-6}$ alkyl; and $R^3$ and $R^4$ represent hydrogen, or $R^3$ and $R^4$ together form a group —S—, —$NR^8$— or —$CH_2$—, and pharmaceutically acceptable derivatives thereof.

Specific compounds that can be used in the formulations of the invention are:

4-Hydroxy-7-[2-[2-[3-(2-phenylethoxy)propylsulphonyl]ethylamino]ethyl]-1,3-benzothiazol-2(3H)-one;

4-Hydroxy-7-[2-[2-[3-(2-phenylethoxy)propoxy]ethylamino]ethyl]-1,3-benzothiazol-2(3H)-one;

N-[2-[2-(4-Hydroxy-2-oxo-3H-1,3-benzothiazol-7-yl)ethylamino]ethyl]-2-(phenylethoxy)ethanesulphonamide;

4-Hydroxy-7-[2-[3-[2-[2-(1-naphthalenyl)ethoxy]ethylsulphonyl]propylamino]ethyl]-1,3-benzothiazol-2(3H)-one; and 3-[2-(4-Hydroxy-2-oxo-3H-1,3-benzothiazol-7-yl)ethylamino]-N-[2-[2-(4-methylphenyl)ethoxyl]ethyl]propanesulphonamide, and pharmaceutically acceptable salts thereof, in particular hydrochloride salts.

Preferred medicaments that can be used in the formulations of the invention include formoterol, terbutaline, budesonide, a formoterol/budesonide combination (e.g., SYMBICORT®), 4-Hydroxy-7-[2-[2-[3-(2-phenylethoxy)propoxy]ethylamino]ethyl]-1,3-benzothiazol-2(3H)-one hydrochloride and 3-[2-(4-Hydroxy-2-oxo-3H-1,3-benzothiazol-7-yl)ethylamino]-N-[2-[2-(4-methylphenyl)ethoxy]ethyl]propanesulphonamide.

Combinations of medicaments may also be employed, for example formoterol/budesonide; formoterol/fluticasone; formoterol/mometasone; salmeterol/fluticasone; formoterol/tiotropium salts; zafirlukast/formoterol, zafirlukast/budesonide; montelukast/formoterol; montelukast/budesonide; loratadine/montelukast and loratadine/zafirlukast.

Further combinations include tiotropium and fluticasone, tiotropium and budesonide, tiotropium and mometasone, mometasone and salmeterol, formoterol and rofleponide, salmeterol and budesonide, salmeterol and rofleponide, and tiotropium and rofleponide.

BRIEF DESCRIPTION OF THE DRAWINGS

FIG. 1 is a graph illustrating data from Example 1, BDP+$C_{12}G_2$ in HFA-134a.

FIG. 3 is a graph illustrating data from Example 3, BDP+$C_{10-12}$ DP 1.4 in HFA-134a.

FIG. 5.1 is a graph illustrating data from Example 5, SD salbutamol sulphate+$C_{12-14}$ DP 1.4 in HFA-134a.

FIG. 5.2 is a graph illustrating data from Example 5, SD salbutamol sulphate+$C_{12-14}$ DP 1.4 in HFA-134a, 1 month stability study.

FIG. 6.1 is a graph illustrating data from Example 6, SD salbutamol sulphate+$C_{12}G_2$ in HFA-134a.

FIG. 6.2 is a graph illustrating data from Example 6, SD salbutamol sulphate+$C_{12}G2$ in HFA-134a, 1 month stability study.

FIG. 7.1 is a graph illustrating data from Example 7, Salbutamol sulphate+$C_{14}$ DP 1.4 in HFA-134a.

FIG. 7.2 is a graph illustrating data from Example 7, Salbutamol sulphate+$C_{14}$ DP 1.4 in HFA-134a, 1 month stability.

FIG. 8 is a graph illustrating data from Control 1, BDP in HFA-134a.

FIG. 10 is a graph illustrating data from Control 3, Spray dried salbutamol sulphate in HFA-134a.

FIG. 11 is a graph illustrating data from Control 3, Spray dried salbutamol sulphate in HFA-134a, 1 month stability study.

FIG. 12.1 is a graph illustrating data from Control 4, Salbutamol sulphate in HFA-134a.

FIG. 12.2 is a graph illustrating data from Control 4, Salbutamol sulphate in HFA-134a, 1 month stability.

Figure 1:
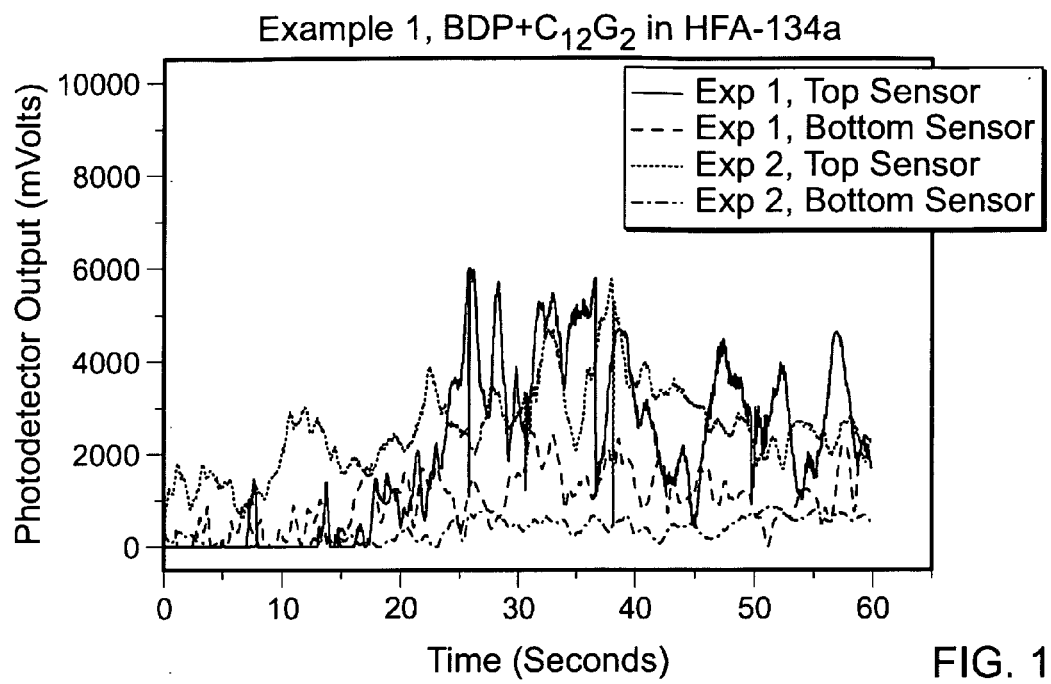
Figure 2:
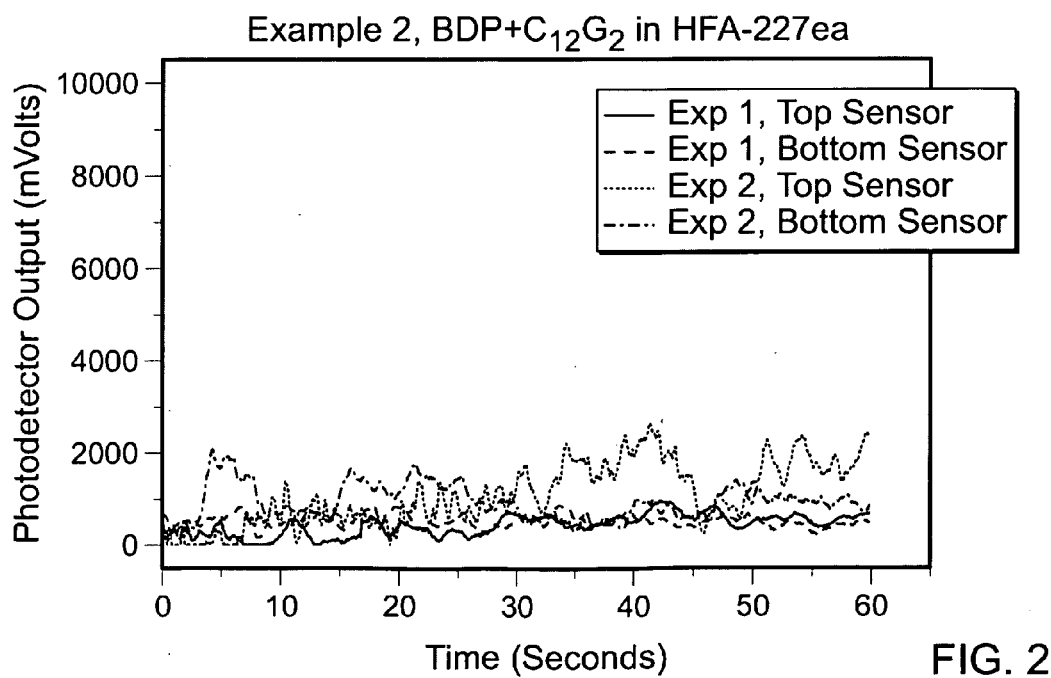
FIG. 2 is a graph illustrating data from Example 2, BDP+$C_{12}G_2$ in HFA-227ea.
Figure 3:
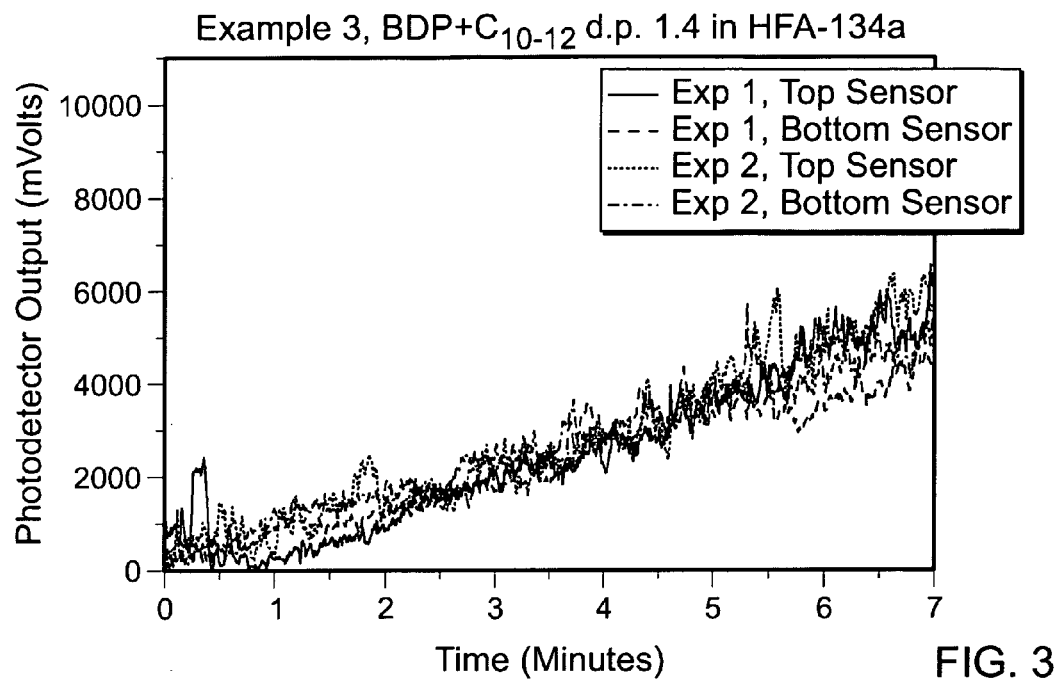
Figure 4:
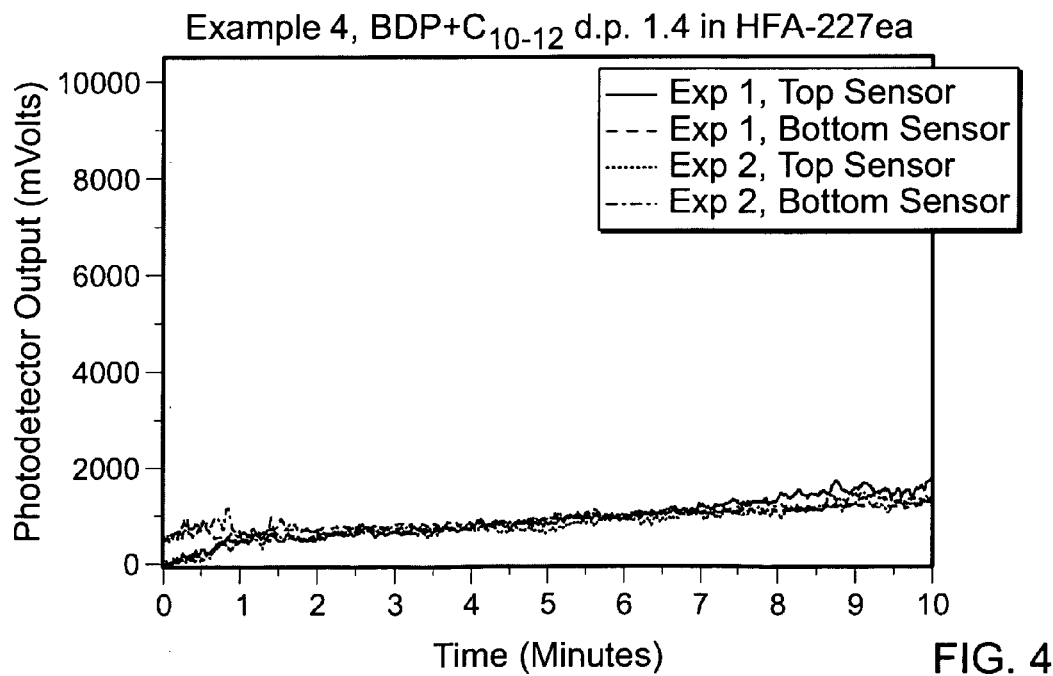
FIG. 4 is a graph illustrating data from Example 4, BDP+$C_{10-12}$ DP 1.4 in HFA-227ea.
Figure 8:
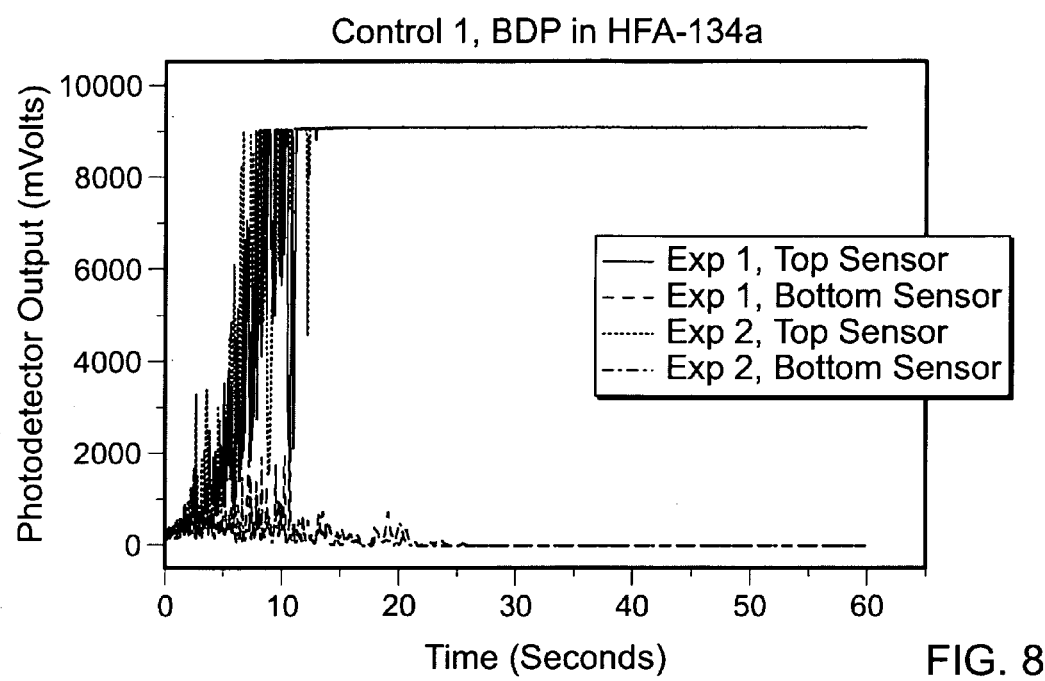
Figure 9:
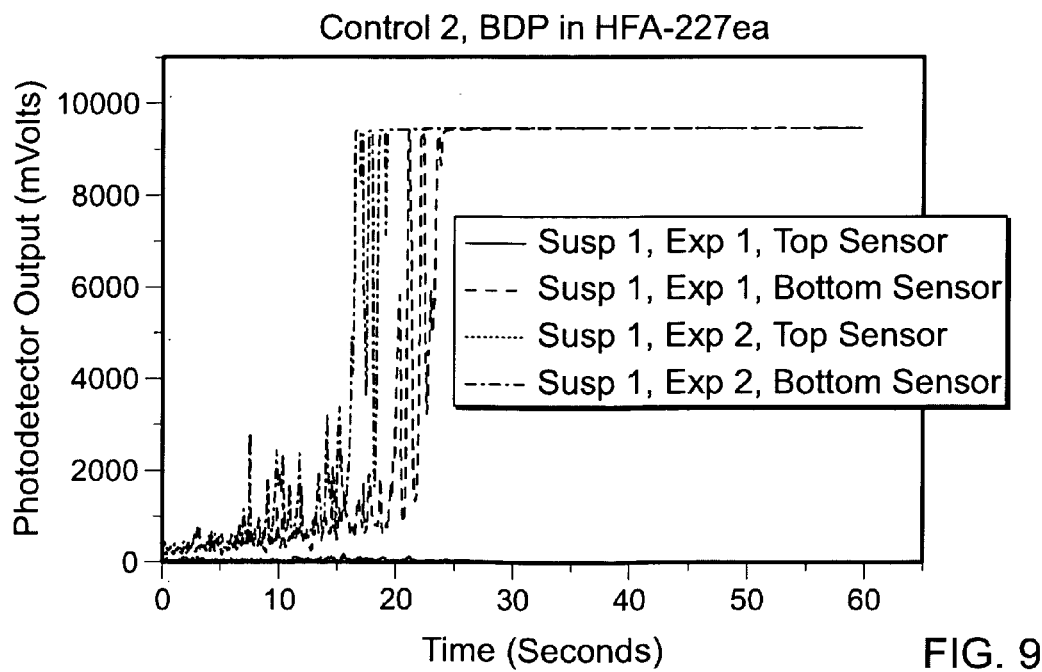
FIG. 9 is a graph illustrating data from Control 2, BDP in HFA-227ea.

The above mentioned compounds may exist as salts and esters as well as solvates (hydrates) and all such forms can be included in the formulations of the invention as are racemates and all stereroisomers of the above compounds where such are possible e.g. (R,R)-formoterol and 22R budesonide.

The amount of surfactant present in the pharmaceutical aerosol formulation of the present invention may range from about 0.00001% by weight of the total weight of the formulation to about 10% by weight of the total weight of the formulation. Preferably, the amount of surfactant present is at least 0.001% by weight Preferably, the amount of surfactant present is up to 1% by weight.

The formulations of the present invention may contain medicament in an amount of from about 0.01% by weight of the total weight of the formulation to about 10% by weight of the total weight of the formulation. Preferably the medicament is present from about 0.01 to about 1.0% by weight.

The medicament may be dissolved or dispersed in the propellant. If the medicament is to be dispersed in the propellant, preferably the medicament consists largely of particles of 400 nm–10 μm, more preferably 400 nm–6 μm, especially 500nm–5 μm. In some circumstances particles of at least 0.001 μm, e.g., at least 0.1 μm, may be desirable.

Preferably at least 50% of the medicament consists of particles within the desired size range. For example at least 60%, preferably at least 70%, more preferably at least 80% and most preferably at least 90% of the medicaments consists of particles within the desired size range.

The medicament for use in the present invention may have to be processed prior to inclusion in the formulations, in order to produce particles in the desired size range. For example the medicament may be milled or micronised, for example using suitable equipment, for example an air jet mill, hammer mill, ball mill or using a microfluidiser. Alternatively, particles in the desired particle range may be obtained by for example spray drying or controlled crystallisation methods, for example crystallisation using supercritical fluids or via an emulsion method, e.g. microfluidisation or homogenisation.

In a particular embodiment, the surfaces of the medicament particles may be modified prior to dispersion, for example by spray drying a solution of drug and surfactant or by adsorption of surfactant onto medicament particles. Further techniques for modification of the surfaces of the medicament particles can also be used such as freeze drying, microfluidising and milling.

Others ingredients may be added into the formulation of the present invention, if desired. Such ingredients may be for example other pharmaceutically active agents, adjuvants, carriers, flavouring agents, buffers, antioxidants, chemical stabilisers, polymers and other surfactants, for example.

The amount of additional ingredients included in the present formulation may be up to 1% w/w.

Dispersion formulations of the present invention maybe prepared for example by adding the alkylpolyglycoside surfactant to propellant by pressure- or cold- filling methods, homogenising, and adding medicament The resultant dispersion may be agitated to ensure dispersion uniformity. Dispersion formulations can also be prepared by co-preparation of particles with excipient, for example by spray drying, to form composite particles.

Solution formulations of the present invention may be prepared by adding the alkylpolyglycoside surfactant and water to propellant by pressure -or cold- filling methods, homogenising, and adding medicament The mixture is agitated, sonicated or heated until the medicament has dissolved.

Aerosol canisters for use with the formulation of the present invention may comprise, for example, a metal can, for example an aluminium can, closed with a metering valve. In a particular embodiment the internal surfaces of the metal can be coated with, for example, a fluoropolymer. Suitable fluoropolymers include PTFE, PFA, and FEP.

The formulation of the present invention is useful for the local or systemic treatment of diseases and may be administered for example via the upper of lower respiratory tract, including the nasal route. As such the present invention also provides said formulation for use in therapy; the use of the formulation in the manufacture of a medicament for the treatment of diseases via the respiratory tract; and a method for the treatment of a patient in need of therapy, comprising administering to said patient a therapeutically effective amount of the formulation of the present invention.

The invention is illustrated in the following examples.

Formulation Preparation

Propellant HFA-134a or HFA-227ea was dispensed chilled (at −55° C.) into an open 400 ml aluminium can. A 1 inch valve was then crimped onto the can and the propellant allowed to return to ambient temperature (20° C.).

Drug (or drug/surfactant mixture) was weighed into a clear polyethyleneterephthalate (PET) vial which was sealed with a non-metering valve. Propellant was then pressure filled through the valve to give the desired drug and surfactant concentrations. The vial was subsequently placed in an ultrasonic bath for one minute to aid dispersion of the particles. 11 samples were prepared according to this method.

EXAMPLE 1

Beclomethasone dipropionate (BDP) B.P (SICOR) was weighed (0.2 g) into a 30 ml glass vial and 20 ml of surfactant solution in water ($C_{12}G_2$, 0.8 g/l) added. The resultant suspension was incubated in a shaking bath at 25° C. for three hours, to allow adsorption of the surfactant to the surface of the drug, and to give a drug-surfactant ratio of 10 mg surfactant/g drug. The suspension was centrifuged (15, 000 rpm, 20 minutes), and the particles of drug-surfactant were separated from the supernatant and dried in an oven at 50° C. for at least 24 hours. The formulation was prepared as described in the preparation paragraph, with the following concentrations:

Beclomethasone dipropionate+$C_{12}G_2$: 0.2%
HFA-134a: to 100%

EXAMPLE 2

Beclomethasone dipropionate B.P. (SICOR) was weighed (0.2 g) into a 30 ml glass vial and 20 ml of surfactant solution in water ($C_{12}G_2$, 0.8 g/l) added. The resultant suspension was incubated in a shaking bath at 25° C. for three hours, to allow adsorption of the surfactant to the surface of the drug, and to give a drug-surfactant ratio of 10 mg surfactant/g drug. The suspension was then centrifuged (15,000 rpm, 20 minutes) and the particles of drug-surfactant were separated from the supernatant and dried in an oven at 50° C. for at least 24 hours. The formulation was prepared as described in the preparation paragraph, with the following concentrations:

Beclomethasone dipropionate+$C_2G_2$: 0.2%
HFA-227ea: to 100%

EXAMPLE 3

Beclomethasone dipropionate B.P (SICOR) was weighed (0.2 g) into a 30 ml glass vial and 20 ml of surfactant solution in water ($C_{10\text{-}12}$ d.p. 1.4, 0.8 g/l) added. The resultant suspension was incubated in a shaking bath at 25° C. for three hours, to allow adsorption of the surfactant to the surface of the drug, and to give a drug-surfactant ratio of 10 mg surfactant/g drug. The suspension was then centrifuged (15,000 rpm, 20 minutes) and the particles of drug-surfactant were separated from the supernatant and dried in an oven at 50° C. for at least 24 hours. The formulation was prepared as described in the preparation paragraph, with the following concentrations:

Beclomethasone dipropionate+$C_{10\text{-}12}$ d.p. 1.4: 0.2%
HFA-134a: to 100%

EXAMPLE 4

Beclomethasone dipropionate B.P (SICOR) was weighed (0.2 g) into a 30 ml glass vial and 20 ml of surfactant solution in water ($C_{10\text{-}12}$ d.p. 1.4, 0.8 g/l) added. The resultant suspension was incubated in a shaking bath at 25° C. for three hours, to allow adsorption of the surfactant to the surface of the drug, and to give a drug-surfactant ratio of 10 mg surfactant/g drug. The suspension was then centrifuged (15,000 rpm, 20 minutes) and the particles of drug-surfactant were separated from the supernatant and dried in oven at 50° C. for at least 24 hours. The formulation was prepared as described in the preparation paragraph, with the following concentrations:

BDP $C_{10\text{-}12}$ d.p. 1.4: 0.2%
HFA-227ea: to 100%

EXAMPLE 5

Microparticles of salbutamol sulphate-$C_{12\text{-}14}$ d.p. 1.4 were prepared by spray drying from solution in water using a Büchi 190 mini spray drier fitted with a 7 mm pneumatic nozzle. A 10% w/v salbutamol sulphate in a solution of 0.06 g/l of $C_{12\text{-}14}$ d.p. 1.4 was spray dried. The conditions and spray drying parameters were: pump speed, 5 ml min$^{-1}$; air flow rate, 800 l h$^{-1}$; aspirator level, 5; inlet temperature, 150° C. (±5° C.) and outlet temperature 80° C. (±5° C.). The material was desiccated immediately after drying. The formulation was prepared as described in the preparation paragraph, with the following concentrations:

Spray dried (SD) salbutamol sulphate+$C_{12\text{-}14}$ d.p. 1.4: 0.08%
HFA-134a: to 100%

EXAMPLE 6

Microparticles of salbutamol sulphate-$C_{12}G_2$ were prepared by spray drying from solution in water using a Büchi 190 mini spray drier fitted with a 7 mm pneumatic nozzle. A 10% w/v salbutamol sulphate in a solution of 0.08 g/l of $C_{12}G_2$ was spray dried. The conditions and spray drying parameters were: pump speed, 5 ml min$^{-1}$; air flow rate, 800 l h$^{-1}$; aspirator level, 5; inlet temperature, 150° C. (±5° C.) and outlet temperature 80° C. (±5° C.). The material was desiccated immediately after drying. The formulation was prepared as described in the preparation paragraph, with the following concentrations:

SD salbutamol sulphate+$C_{12}G_2$: 0.08%
HFA-134a: to 100%

EXAMPLE 7

Salbutamol sulphate was weighed (0.2 g) into a 30 ml glass vial and 20 ml of surfactant solution in $CH_2Cl_2$ ($C_{14}$ d.p. 1.4, 0.6 g/l) added. The resultant suspension was incubated in a shaking bath at 25° C. for three hours, to allow adsorption of the surfactant to the surface. This was then filtered under vacuum and the particles of drug-surfactant collected and dried overnight at room temperature. The formulation was prepared as described in the preparation paragraph, with the following concentrations:

Salbutamol sulphate+$C_{14}$ d.p. 1.4: 0.08%
HFA-134a: to 100%
7

Control 1:
The formulation was prepared as described in the preparation paragraph, with the following concentrations:
Beclomethasone dipropionate: 0.2%
HFA-134a: to 100%

Control 2:
The formulation was prepared as described in the preparation paragraph, with the following concentrations:
Beclomethasone dipropionate: 0.2%
HFA-227ea: to 100%

Control 3:
Microparticles of salbutamol sulphate were prepared by spray drying from an aqueous solution, using a Büchi 190 mini spray drier fitted with a 7 mm pneumatic nozzle. A 10% w/v salbutamol sulphate solution in water was used. The spray drying parameters were: pump speed 5 ml min$^{-1}$; air flow rate 800 l h$^{-1}$; aspirator level 5; inlet temperature 150° C. (±5° C.) and outlet temperature 80° C. (±5° C.). The material was desiccated immediately after drying. The formulation is then prepared as described in the preparation paragraph, with the following concentrations:
SD salbutamol sulphate: 0.08%
HFA-134a: to 100%

Control 4:
The formulation was prepared as described in the preparation paragraph, with the following concentrations:
Salbutamol sulphate: 0.08%
HFA-134a: to 100%

The following table summarises the list of samples prepared:

| Sample | Material | HFA | Surfactant/drug ratio |
|---|---|---|---|
| 1 | BDP + $C_{12}G_2$ | 134a | 10 mg/1 g |
| 2 | BDP + $C_{12}G_2$ | 227ea | 10 mg/1 g |
| 3 | BDP + $C_{10\text{-}12}$ d.p. 1.4 | 134a | 10 mg/1 g |
| 4 | BDP + $C_{10\text{-}12}$ d.p. 1.4 | 227ea | 10 mg/1 g |
| 5 | SD salbutamol sulphate + $C_{12\text{-}14}$ d.p. 1.4 | 134a | 0.6 mg/1 g |
| 6 | SD salbutamol sulphate + $C_{12}G_2$ | 134a | 0.8 mg/1 g |

-continued

| Sample | Material | HFA | Surfactant/drug ratio |
|---|---|---|---|
| 7 | Salbutamol sulphate + $C_{14}$ d.p. 1.4 | 134a | 0.8 mg/1 g |
| Control 1 | BDP | 134a | N/A |
| Control 2 | BDP | 227ea | N/A |
| Control 3 | SD salbutamol sulphate | 134a | N/A |
| Control 4 | Salbutamol sulphate | 134a | N/A |

Product Evaluation:

OSCAR Analysis (Optical Suspension Characterisation)

In this technique, two matched pairs of infra-red emitter/detector probes are directed at the clear PET vial. The upper detectors were placed 3 mm below the suspension surface and the lower detectors placed at 3 mm from the bottom of the vial. The infrared probes detect any changes in light transmission through the suspension. Measurement starts automatically when the upper light beam is broken when the vial is inserted. A personal computer then processes the voltage signal and a profile of light transmission is obtained. If the suspension is stable then the transmitted signal will be low. However, if the suspension is unstable and has either settled out or creamed the light transmission will be high. A basic measurement of how rapidly the sample sediments or creams is given by how long it takes the upper (if sedimenting) or lower (if creaming) detector signal to change and reach an equilibrium reading. Further to this, if the fluctuation of the signal with time is great, this is an indication that the sample is flocculating (aggregate size is increasing) and indicates that the suspension is unstable.

Results for the previous samples are listed below. All samples show better stability characteristics than the control samples. Typically, stability times increase from a second timescale to minutes. The presence of the APG does improve substantially the characteristics of the pMDI suspension. The samples also show very good characteristics on storage as demonstrated from the 1 month stability data.

Samples 1 and 3 (BDP with APGs in HFA-134a) can be compared with control 1. In both cases the stability of the suspension increases from 10 seconds for the control sample to over one minute for the samples with APGs.

Samples 2 and 4 (BDP with APGs in HFA-227ea) can be compared with control 2. The stability times increase from 20 seconds to well over 10 minutes. In the case of sample 2, the stability is above 60 minutes, indicating an extremely slow creaming rate.

The salbutamol sulphate samples show similar trends, although the timescale for improvements are different. In this case, the best indicators of improvements are the profiles after one month's storage. At the initial timepoint, the suspension stability of salbutamol sulphate formulated with APGs (samples 5 and 6—SD salbutamol sulphate with APGs in HFA-134a) are not as good as the control (Control 3). However after one month's storage, the Control has deteriorated but the suspensions formulated with APGs have improved significantly.

Sample 7 (salbutamol sulphate with APG in HFA-134a) is to be compared with control 7. Again, the presence of the APG improves suspension stability by increasing the creaming times, with a particularly beneficial influence after storage.

Visual Assessment

Visual assessment was carried out on the OSCAR samples. After removing the samples from the ultrasonic bath, observations were made to assess the degree of flocculation of the drug suspensions and also the kinetics of sedimentation or creaming.

| Sample | Material | HFA | Flocculation? | Sedimentation/creaming |
|---|---|---|---|---|
| 1 | BDP + $C_{12}G_2$ | 134a | No | Slow |
| 2 | BDP + $C_{12}G_2$ | 227ea | No | Slow |
| 3 | BDP + $C_{10-12}$ d.p. 1.4 | 134a | No | Very slow |
| 4 | BDP + $C_{10-12}$ d.p. 1.4 | 227ea | No | Very slow |
| 5 | SD salbutamol sulphate + $C_{12-14}$ d.p. 1.4 | 134a | Yes | Fast |
| 6 | SD salbutamol sulphate + $C_{12}G_2$ | 134a | Yes | Fast |
| 7 | Salbutamol sulphate + $C_{14}$ d.p. 1.4 | 134a | No | Very slow |
| Control 1 | BDP | 134a | Yes | Very fast |
| Control 2 | BDP | 227ea | Yes | Very fast |
| Control 3 | SD salbutamol sulphate | 134a | Yes | Slow |
| Control 4 | Salbutamol sulphate | 134a | Yes | Fast |

For all systems, the presence of APG improved the suspension characteristics. Initial observations are summarised in the previous table. After one month storage, the spray dried salbutamol samples showed a definite improvement compared to the control samples (Control 3).

One month stability:

| Sample | Material | HFA | Flocculation? | Sedimentation/creaming |
|---|---|---|---|---|
| 5 | SD salbutamol sulphate + $C_{12-14}$ d.p. 1.4 | 134a | Yes | slow |
| 6 | SD salbutamol sulphate + $C_{12}G_2$ | 134a | Yes | Slow |
| Control 3 | SD salbutamol sulphate | 134a | Yes | Fast |

IGC

Surface energy of the drug and the drug surfactant particles was measured by inverse gas chromatography. A silanised U-shaped column (3 mm internal diameter, 30 cm length) was packed with approximately 400 mg of the test powder and dried under nitrogen for 24 hours at 50° C. The powder bed was then allowed to settle for 24 hours at 35° C. (temperature used during the experiments) under nitrogen. The test probes used were: hexane, heptane, octane, chloroform, $CCl_4$, benzene, acetone, tetrahydrofuran, ethyl acetate and diethyl ether. One ml of air containing a minute concentration of each gaseous probe was injected into the column and the retention time measured.

| MATERIAL | $\gamma s^D$ MJ/M$^2$ (n = 3) | Kd/Ka |
|---|---|---|
| BDP | 52.34 (1.09) | 8.82 |
| BDP + $C_{12} G_2$ | 50.25 (1.33) | 6.09 |
| BDP + $C_{10-12}$ d.p. 1.4 | 36.30 (1.62) | 2.15 |
| Salbutamol sulphate | 43.27 (0.67) | 1.76 |
| Salbutamol sulphate + $C_{14}$ d.p. 1.4 | 38.23 (0.36) | 2.61 |

What is claimed is:

1. An inhalable pharmaceutical aerosol formulation comprising a hydrofluoroalkane propellant, a medicament and a surfactant that is an alkyl-polyglycoside of formula I:

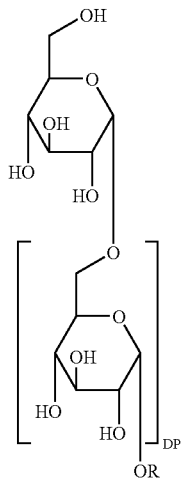

or a derivative thereof;

wherein DP is the average degree of polymerisation and R is an alkyl chain or a mixture of alkyl chains having a chain length of from 6 to 22 carbon atoms; wherein:

R is 2-ethyl-1-hexyl and DP is 1.6; or

R is a mixture of $C_8$ and $C_{10}$ alkyl chains in a ratio of 60 $C_8$:40 $C_{10}$ and DP is 1.5; or R is a mixture of $C_{16}$ and $C_{18}$ alkyl chains and DP is 1.2–1.3; or R is a mixture of $C_{20}$ and $C_{22}$ alkyl chains and DP is 1.2–1.3; or R is $C_{10}$ and DP is 2.7; or R is a mixture of $C_{10}$ and $C_{12}$ alkyl chains and DP is 1.4; or R is a mixture of $C_{12}$ and $C_{14}$ alkyl chains and DP is 1.4; or the alkylpolyglycoside is n-dodecyl β-D-maltoside ($C_{12}G_2$).

2. A formulation according to claim 1 wherein:

R is 2-ethyl-1-hexyl and DP is 1.6; or

R is a mixture of $C_8$ and $C_{10}$ alkyl chains in a ratio of 60 $C_8$:40 $C_{10}$ and DP is 1.5; or R is $C_{10}$ and DP is 2.7; or R is a mixture of $C_{10}$ and $C_{12}$ alkyl chains and DP is 1.4.

3. A formulation according to claim 1 wherein the propellant is HFA-134a or HFA-227ea or a mixture thereof.

4. A formulation according to claim 1 wherein the medicament is a β2-adrenoreceptor agonist, an anticholinergic bronchodilator, or a 16,17-acetal of a pregnane derivative.

5. A formulation according to claim 1 wherein the medicament is formoterol, terbutaline, budesonide or a formoterol/budesonide combination.

6. A formulation according to claim 1 wherein the medicament is a compound of formula:

Ar-CH$_2$—CH$_2$—NH—CR$^1$R$^2$-A-Z or a pharmaceutically acceptable salt, ester or solvate thereof;

wherein Ar represents a group:

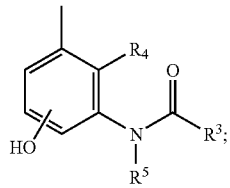

A represents a straight or branched $C_{1-12}$ alkylene chain that is interrupted or terminated by one or more groups selected from —S—, —SO—, SO$_2$—, —O—, SO$_2$NH, NHSO$_2$, CR$^6$R$^7$, phenylmethyne, —NH—, —CONH—, —NHCO— and —NHCONH—;

Z represents an aryl group of five or six atoms in a single ring system, which optionally contains from 1 to 3 heteroatoms selected from N, O and S, which single ring system is optionally substituted to form a multiple fused ring system of up to 10 atoms, the aryl group being optionally substituted by one or more groups selected from —OH, halogen, $C_{1-6}$ alkyl, $C_{1-6}$ alkoxy, =O, —NR$^8$R$^9$, and —NO$_2$; or Z represents a $C_{3-12}$ cycloalkyl group containing from 1 to 3 heteroatoms selected from N, O and S, optionally substituted by one or more groups selected from —OH, halogen, $C_{1-6}$ alkyl, $C_{1-6}$ alkoxy, =O, —NH$_2$ and NO$_2$;

R$^1$, R$^2$, R$^5$, R$^6$, R$^7$, R$^8$ and R$^9$ each independently represent hydrogen or $C_{1-6}$ alkyl; and R$^3$ and R$^4$ represent hydrogen, or R$^3$ and R$^4$ together form a group that is —S—, —NR$^8$— or —CH$_2$—.

7. A formulation according to claim 1 wherein the medicament is:

4-hydroxy-7-[2-[2-[3-(2-phenylethoxy)propylsulphonyl]ethylamino]ethyl]-1,3-benzo-thiazol-2(3H)-one;

4-hydroxy-7-[2-[2-[3-(2-phenylethoxy)propoxy]ethylamino]ethyl]-1,3-benzo-thiazol-2(3H)-one;

N-[2-[2-(4-hydroxy-2-oxo-3H-1,3-benzothiazol-7-yl)ethylamino]ethyl]-2-(phenyl-ethoxy)ethanesulphonamide;

4-hydroxy-7-[2-[3-[2-[2-(1-naphthalenyl)ethoxy]ethylsulphonyl]propylamino]ethyl]-1,3-benzothiazol-2(3H)-one;

3-[2-(4-hydroxy-2-oxo-3H-1,3-benzothiazol-7-yl)ethylamino]-N-[2-[2-(4-methylphenyl)ethoxy]ethyl]propanesulphonamide; or a pharmaceutically acceptable salt, ester or solvate thereof.

8. A formulation according to claim 1 wherein the medicament is a combination of formoterol and budesonide, formoterol and fluticasone, formoterol and mometasone, salmeterol and fluticasone, formoterol and tiotropium salt, zafirlukast and formoterol, zafirlukast and budesonide, montelukast and formoterol, montelukast and budesonide, loratadine and montelukast, loratadine and zafirlukast, tiotropium and fluticasone, tiotropium and budesonide, tiotropium and mometasone, mometasone and salmeterol, formoterol and rofleponide, salmeterol and budesonide, salmeterol and rofleponide, or tiotropium and rofleponide.

9. A formulation according to claim 1 wherein the amount of surfactant present is at least 0.001% by weight.

10. A formulation according to claim 1 wherein the amount of medicament present is from 0.01 to 1.0% by weight.

11. An inhalable medicinal aerosol containing a formulation according to claim 1.

12. A method of treatment for a patient in need of therapy, comprising administering to said patient a therapeutically effective amount of a formulation according to claim 1.

13. A method of treatment for a patient in need of therapy, comprising administering to said patient via inhalation a therapeutically effective amount of a formulation according to claim 2.

14. A method of treatment for a patient in need of therapy, comprising administering to said patient via inhalation a therapeutically effective amount of a formulation according to claim 3.

15. A method of treatment for a patient in need of therapy, comprising administering to said patient via inhalation a therapeutically effective amount of a formulation according to claim 4.

16. A method of treatment for a patient in need of therapy, comprising administering to said patient via inhalation a therapeutically effective amount of a formulation according to claim 5.

17. A method of treatment for a patient in need of therapy, comprising administering to said patient via inhalation a therapeutically effective amount of a formulation according to claim 6.

18. A method of treatment for a patient in need of therapy, comprising administering to said patient via inhalation a therapeutically effective amount of a formulation according to claim 7.

19. A method of treatment for a patient in need of therapy, comprising administering to said patient via inhalation a therapeutically effective amount of a formulation according to claim 8.

20. A method of treatment for a patient in need of therapy, comprising administering to said patient via inhalation a therapeutically effective amount of a formulation according to claim 9.

21. A method of treatment for a patient in need of therapy, comprising administering to said patient via inhalation a therapeutically effective amount of a formulation according to claim 10.

22. An aerosol canister containing a formulation according to claim 1.

23. An aerosol canister containing a formulation according to claim 2.

24. An aerosol canister containing a formulation according to claim 3.

25. An aerosol canister containing a formulation according to claim 4.

26. An aerosol canister containing a formulation according to claim 5.

27. An aerosol canister containing a formulation according to claim 6.

28. An aerosol canister containing a formulation according to claim 7.

29. An aerosol canister containing a formulation according to claim 8.

30. An aerosol canister containing a formulation according to claim 9.

31. An aerosol canister containing a formulation according to claim 10.

* * * * *